United States Patent
Blaler et al.

(10) Patent No.: US 6,323,365 B1
(45) Date of Patent: Nov. 27, 2001

(54) ACTIVE DERIVATIVE OF VALPROIC ACID FOR THE TREATMENT OF NEUROLOGICAL AND PSYCHOTIC DISORDERS AND A METHOD FOR THEIR PREPARATION

(75) Inventors: Meir Blaler; Boris Yagen, both of Jerusalem; Niv Papo, Raanana, all of (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/628,016

(22) Filed: Jul. 28, 2000

(51) Int. Cl.$^7$ .......................... C07C 233/05; A61K 31/16
(52) U.S. Cl. ........................ 564/224; 514/629; 564/143
(58) Field of Search .................................. 564/224, 143; 514/629

(56) References Cited
U.S. PATENT DOCUMENTS 4,230,688 * 10/1980 Roswell et al. .

* cited by examiner

*Primary Examiner*—Shailendra Kumar
(74) *Attorney, Agent, or Firm*—Lowe Hauptman Gilman & Berner, LLP

(57) ABSTRACT

The invention relates to pharmaceutical compositions and methods of preparation thereof suitable for the treatment of neurological, affective and psychotic disorders and for the treatment of pain and migraine comprising as an active ingredient an effective amount of 2-hydroxylpropyl valpormide and a pharmaceutically acceptable carrier or diluent. In a broader sense, the invention concerns 2-hydroxylpropyl valpromide (HP-VPD) of the formula:

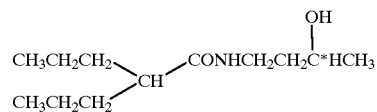

useful for the treatment of neurological, psychotic and affective disorders, such as convulsions and epilepsy, and for the treatment of pain and migraine.

12 Claims, No Drawings

ACTIVE DERIVATIVE OF VALPROIC ACID FOR THE TREATMENT OF NEUROLOGICAL AND PSYCHOTIC DISORDERS AND A METHOD FOR THEIR PREPARATION

FIELD OF THE INVENTION

The present invention relates to compounds useful for the treatment of neurological and psychotic disorders. More specifically the present invention relates to a novel compound 2-hydroxylpropyl valpromide (HP-VPD), especially to its (S)-enantiomer, as a new antiepileptic and CNS active compound, and to pharmaceutical compositions containing said compounds as an active ingredient. 2-hydroxylpropyl valpromide is shown to be more potent than valproic acid (VPA). The present invention further relates to a method for the synthesis of said compound and more specifically to a stereoselective synthesis for obtaining the (S) or (R) enantiomers of said compound.

BACKGROUND OF THE INVENTION

Epilepsy is a common and chronic disease which affects about 1% of the global population. Although a number of new antiepileptic drugs (AEDs) have been introduced recently in Europe and the U.S., at present there are only four major AEDs: phenobarbital, phenytoin, carbamazerpine and valproic acid. With the existing medications, about 25% of epileptic patients are still not seizure-free even if the therapy is optimally managed (R. H. Levy and D. D. Shen. in Levy R. H. et al (eds) *Antiepileptic Drugs*, 4th edition, Raven Press, N.Y. 1995 pp. 605–620 and other chapters on valproate therein). In addition, therapy with existing AEDs is associated with side effects which increase the morbidity of epileptic patients.

Antiepileptic drug therapy treats the symptoms (seizure) while the cause of the epilepsy in many cases remains unknown. Since AEDs have to be administered repetitively as chronic treatment in antiepileptic therapy, the issues of side effects and drug toxicity are cardinal. Therefore, efforts are on-going to develop new and potent AEDs with minimal side effects (Bialer M. et al *Pharm. World Sci.* 16: 2–6, 1994).

Valproic acid (VPA-I), one of the major antiepileptic drugs (AEDs) is associated with teragenecity and hepatotoxicity. So far, world wide 132 patients have died from VPA-associated liver failure or fatal hepatotoxicity. A strong association exists between maternal use of antiepileptic drugs (AEDs) during pregnancy and birth defects in offspring. The overall malformation rate is 11.1% in the offspring of untreated epileptic mothers and 4.8% in those of the general population. VPA treatment during pregnancy may result in a 5- to 10-fold increase in the incidence of neural tube defects compared with incidence in the general population.

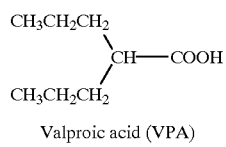

Valproic acid (VPA)

The present invention provides a new CNS-active amide derivative of VPA, the compound 2-hydroxypropyl valpromide (HP-VPD), which is more potent as an antiepileptic than VPA.

As a chiral molecule with one asymmetric carbon racemic HP-VPD is a mixture of two enantiomers (R)-HP-VPD (II) and (S)-HP-VPD (III). Since HP-VPD is a chiral molecule its individual optical isomers may have different pharmacokinetics, pharmacodynamics potency and teratogenecity.

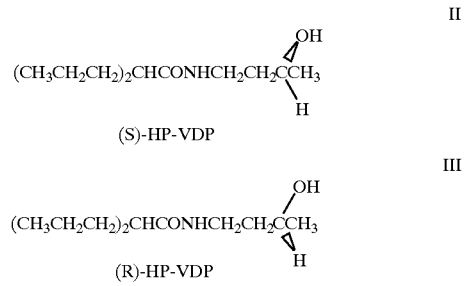

The two enantiomers of HP-VPD were prepared by a stereospecific synthesis and their antiepileptic activity and neurotoxicity was analyzed in comparison to racemic HP-VPD and VPA (I). Individual enantiomers and racemic HP-VPD were screened following oral administration to rats for their anticonvulsant activity and neuriotoxicity at the NIH Epilepsy Branch by the maximal electoshock (MES) test which measures seizure spread; by the subcutaneous metrazol (sc Met) test, which measures seizure threshold; and by the rotorod ataxia test, which assesses minimal neurotoxicity.

Anticonvulsant activity at the maximal electoshock (MES) test has been associated with antiepileptic activity in complex partial epilepsy which is common epilepsy among therapy-resistant (refractory) epileptic patients. The results of the study show that the (S)-HP-VDP in particular, has a potential to become a new efficient antiepileptic drug.

The fact that unlike VPA, different valproylamide analogue were found to be non-teratogenic in animal studies (H. Nau and A. G. Hendricks *ISI Atlas Sci*: Pharmacol. 1, 52–56, 1987 and M. Radatz et. al. *Epilepsy Res.* 20:41–49, 1998) give the HP-VPD the potential to be non-teratogenic entity.

SUMMARY OF THE INVENTION

The present invention relates to 2-hydroxylpropyl valpromide (HP-VPD)

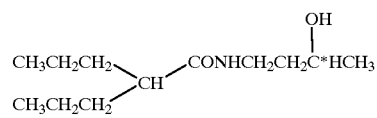

as an active compound for the treatment of neurological and psychotic disorders, for the treatment of epilepsy and convulsions and for the treatment of pain and migraine. The compound of the present invention can be a racemic mixture or in the form of pure stereisomers, or any other mixture thereof The present invention further relates to pharmaceutical compositions for administration to a mammal, and in particular to humans, comprising an effective amount of said active ingredient and any pharmaceutically acceptable carrier or diluent, for the treatment of neurological and affective and psychotic disorders and for the treatment of pain and migraine.

Said pharmaceutical composition according are especially useful controlling epileptic seizures, febrile convulsions and convulsions precipitated by an irritative lesion in the brain and to for treating bipolar diseases.

The present invention further relates to a method for the synthesis of said compound and more specifically to a stereoselective synthesis for obtaining the (S) or (R) enantiomers of said compound.

EXPERIMENTAL

The two enantiomers of HP-VPD were synthesized by a stereospecific synthesis and their antiepileptic activity and neurotoxicity was analyzed in comparison to racemic HP-VPD and VPA (I). Individual enantiomers and racemic HP-VPD were screened following oral administration to rats for their anticonvulsant activity and neurotoxicity at the NIH Epilepsy Branch.

Synthesis of (S)-, (R)- and rac-2-hydroxypropyl Valpromide (HP-VPD)

2-hydroxypropyl valpromide was obtained from the reaction between valpropyl chloride (V) and 1-amino-2-propanol (VI)

$$CH_3CH(OH)CH_2NH_2 \quad V$$

$$\begin{array}{c} CH_3CH_2CH_2 \\ \diagdown \\ CH-COCl \\ \diagup \\ CH_3CH_2CH_2 \end{array} \quad VI$$

by the following procedure:

Rac-1-amino-2-propanol (5 g., 67 mmole), and 30 ml of dry dichloromethane were stirred in a 250 ml round-bottomed flask at 0° C. for 15 min.

Valproyl chloride (5 g., 30 mmole) in 20 ml of dry dichloromethane was added dropwise to this solution over a period of 20 min. The mixture was stirred at 0° C. for an hour after the completion of the addition, then extracted three times with 100 ml of ethyl acetate. The organic extracts were combined, dried with $MgSO_4$, filtered and evaporated. A crude white solid was obtained. Recrystallization from an ethyl acetate-petrol ether (2:3 v/v) mixture yielded 4.7 g. (77%) of analytically pure rac-N-(2-OH-propyl)valpromide (HP-VPD).

The synthesis of (S) and (R) N-(2-OH-propyl)valpromide (HP-VPD) was identical to that used for the synthesis of racemic-N-(2-OH-propyl)valpromide (HP-VPD) starting from (S) or (R) 1-amino-2-propanol respectively. For the S enantiomer, the yield was 4.7 g. (77%) and for the R enantiomer, the yield was 3.8 g. (62%).

Following is analytical data: M.P: 78° C.; Elemental Analysis ($C_{11}H_{23}NO_2$): Calc.: C: 65.67%; H: 11.44%; N: 6.97% Found: C: 65.67%; H: 11.16%; N: 6.73% $^1$H NMR ($CDCl_3$,1%TMS): d (ppm) 5.86 (s, br., 1H), 3.92 (s, br., 1H), 3.45 (m, 1H), 3.14 (m, 1H), 2.66 (s, br., 1H), 2.06 (m, 1H), 1.27–1.68 (m, 8H), 1.19 (d, 3H), 0.89 (t, 6H).

IR ($cm^{-1}$): 3297, 3097, 2929, 2874, 1643, 1558, 1460, 1089.

Anticonvulsant Activity

The screening procedure involved the following (R. J. Porter et. al. *Clev. Clin. Q.* 51: 293–305, 1984): 1) the maximal electroshock (MES) test, which measures seizure spread; 2) the subcutaneous metrazol (sc Met) test, which measures seizure threshold; and 3) the rotorod ataxia test, which assesses minimal neurotoxicity.

The pharmacodynamic (anticonvulsant activity and neurotoxicity) results are shown in Table 1.

In the MES test, racemic HP-VPD was five times more potent than VPA, whereas (S)-HP-VPD (III) was more than two times more potent than (R)-HP-VPD (II) leading to a stereoselective index (SI) of 2.4.

TABLE I

Anticonvulsant activity ($ED_{50}$) and neurotoxicity ($TD_{50}$) obtained following oral administration of racemic (HP-VPD) and individual enantiomers of N-(2-Hydroxypropyl)valpromide (HP-VPD) to rats in comparision to VPA.

|  | VPA | HP-VPD (rac) | (S)-HP-VPD (II) | (R)-HP-VPD (III) | SI |
|---|---|---|---|---|---|
| MES | 490 | 92 | 48 | 117 | 2.4 |
| sc Met | 180 | >250 | — | — | — |
| Neurotox. | 280 | >250 | >650 | >500 | — |
| PI-MES | 0.6 | >2.7 | >13.5 | >4.3 | — |
| PI-sc Met | 1.6 | — | — | — | — |

*ED50 & TD50 (mg/kg)
*SI = (R)-HP-VPD/(S)-HP-VPD
*PI (protective index): TD50/ED50

All chemicals and solvents used were purchased from Aldrich, Milwaukee, Wis. USA and were analitical grade. Compounds II–III and the racemate were synthesized according to the methods as described before and their chemical structures and purity was confirmed by elemental microanalysis and NMR.

What is clamed is:

1. 2-hydroxylpropyl valpromide (HP-VPD) of the formula:

$$\begin{array}{c} CH_3CH_2CH_2 \\ \diagdown \\ CH-CONHCH_2CH_2C^*HCH_3 \\ \diagup \quad\quad\quad\quad\quad\quad\quad\quad | \\ CH_3CH_2CH_2 \quad\quad\quad\quad\quad\quad OH \end{array}$$

useful for the treatment of neurological, psychotic and affective disorders, such as convulsions and epilepsy, and for the treatment of pain and migraine.

2. The (S) optical isomer of the compound as defined in claim 1.

3. The (R) optical isomer of the compound as defined in claim 1.

4. Pharmaceutical composition for the treatment of neurological, affective and psychotic disorders and for the treatment of pain and migraine comprising as an active ingredient an effective amount of 2-hydroxylpropyl valpromide and a pharmaceutically acceptable carrier or diluent.

5. Pharmaceutical composition according to claim 4 wherein the active ingredient is the (S) or (R) optical isomers of the compound of claim 1.

6. Pharmaceutical composition according to claim 4 for controlling epileptic seizures, febrile convulsions and convulsions precipitated by an irritative lesion in the brain and to for treating bipolar diseases, chronic pain, headaches and migraines.

7. A method for obtaining 2-hydroxylpropyl valpromide or its optical isomers by reacting valproyl chloride and 1-amino-2-propanol or its corresponding optical isomers.

8. A method according to claim 7 for obtaining 2-hydroxylpropyl valpromide comprising of the following steps;

(a) Stirring 1-amino-2-propanol and dry dichloromethane at approximately 0° C.;

(b) dropwise adding valproyl chloride dissolved in dry dichloromethane into the mixture of step (a) at approximately 0° C.;

(c) extracting the mixture obtained in (b) with ethyl acetate;

(d) drying the organic extract obtained in (c), filtering and evaporating;

(e) re-crystallizing the solid obtained in (d) from ethyl acetate-petrol ether to obtain pure HP-VPD.

9. A method for the preparation of (S)-enantiomer or (R)-enantiomer of 2-hydroxylpropyl valpromide (HP-VPD) comprising of the following steps;

(a) stirring (R) or (S) 1-amino-2-propanol and dry dichloromethane at approximately 0° C.;

(b) dropwise adding valproyl chloride dissolved in dry dichloromethane into the mixture of step (a) at approximately 0° C.;

(c) extracting the mixture obtained in (b) with ethyl acetate;

(d) drying the organic extract obtained in (c), filtering and evaporating;

(e) recrystalizing the solid obtained in (d) from ethyl acetate-petrol ether to obtain (R) or (S) HP-VPD respectively.

10. A method of treating neurological, affective and psychotic disorders in a mammal in need of such treatment by administering to the mammal an effective amount of the composition as defined in claim 3.

11. A method for controlling epileptic seizures, febrile convulsions and convulsions precipitated by an irritative lesion in the brain in a mammal in need of such treatment by administering to the mammal an effective amount of the pharmaceutical composition as defined in claim 4.

12. A method of treating bipolar diseases, chronic pain, headaches and migraines, in a mammal in need of such treatment by administering to the mammal an effective amount of the pharmaceutical composition as defined in claim 4.

* * * * *